(12) United States Patent
Röding et al.

(10) Patent No.: US 9,483,440 B2
(45) Date of Patent: Nov. 1, 2016

(54) METHOD AND SYSTEM FOR DISPERSION MEASUREMENTS

(75) Inventors: Magnus Röding, Fjärås (SE); Mats Rudemo, Stockholm (SE); Kevin Braeckmans, Daknam (BE); Stefaan De Smedt, Mariakerke (BE); Joseph De Meester, Ghent (BE); Hendrik Deschout, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 804 days.

(21) Appl. No.: 13/809,011

(22) PCT Filed: Jul. 6, 2011

(86) PCT No.: PCT/EP2011/061443
§ 371 (c)(1),
(2), (4) Date: Jan. 8, 2013

(87) PCT Pub. No.: WO2012/004320
PCT Pub. Date: Jan. 12, 2012

(65) Prior Publication Data
US 2013/0116935 A1 May 9, 2013

(30) Foreign Application Priority Data
Jul. 9, 2010 (GB) .................................. 1011590.5

(51) Int. Cl.
| | |
|---|---|
| *G06F 17/00* | (2006.01) |
| *G01N 15/06* | (2006.01) |
| *G01N 15/14* | (2006.01) |
| *G01N 15/02* | (2006.01) |
| *G01N 15/10* | (2006.01) |

(52) U.S. Cl.
CPC ............ *G06F 17/00* (2013.01); *G01N 15/06* (2013.01); *G01N 15/1463* (2013.01); *G01N 2015/025* (2013.01); *G01N 2015/1075* (2013.01); *G01N 2015/1497* (2013.01)

(58) Field of Classification Search
USPC .......................................................... 702/29
See application file for complete search history.

(56) References Cited

U.S. PATENT DOCUMENTS 4,854,705 A 8/1989 Bachalo

FOREIGN PATENT DOCUMENTS

EP 0 359 681 A2 3/1990

OTHER PUBLICATIONS

Matthias Mandø, On the modelling of motion of non-spherical particles in two-phase flow, Aalborg University, Institute of Energy Technology Pontoppidanstræde 101, DK-9220, Aalborg East, Denmark, 6th International Conference on Multiphase Flow, ICMF 2007, Leipzig, Germany, Jul. 9-13, 2007, pp. 1-14.*
C. S. Simmons, Stochastic-convective transport with nonlinear reaction: Mathematical framework, Water Resources Research, vol. 31, No. 11, pp. 2675-2688, Nov. 1995, p. 2675-2688.*

(Continued)

*Primary Examiner* — Tung Lau
(74) *Attorney, Agent, or Firm* — Bacon & Thomas, PLLC

(57) ABSTRACT

A method for determining a size or shape related parameter of an effective observation volume for an observation technique for particles undergoing at least partially stochastic motion in a dispersion is based on a time-series of observations. The method involves determining one or more time-dependent characteristics of the dispersion or its particles based on the time-series of observations, determining at least one stochastic motion-related parameter representative for the at least partially stochastic motion of at least one particle in the dispersion, and determining a size or shape related parameter of the effective observation volume by modeling of the at least partially stochastic motion of the particle movement in the dispersion, the modeling taking into account the at least one stochastic motion-related parameter and the determined one or more characteristics.

20 Claims, 12 Drawing Sheets

(56) References Cited

OTHER PUBLICATIONS

F.J.Bermejo, Multiple time scales in the microscopic dynamics of simple and complex liquids as studied by radiation scattering, Condensed Matter Physics 2008, vol. 11, No. 1(53), pp. 95-106.*
Tobias Strömgren in Modelling of turbulent gas-particle flow, Universitetsservice US-AB, Stockholm 2008, 34 pages.*

Andrew Malloy et al., "NanoParticle Tracking Analysis—The Halo™ System," Part. Part. Syst. Charact. 23 (2006), pp. 197-204, Wiley-VCH Verlag GmbH /7 Co. KGaA, Weinheim, XP-002659889.
Shangfeng Du et al., "Measuring number-concentractions of nanoparticles and viruses in liquids on-line," J Chem Technol Biorechnol 2010; 85: 1223-1228, Wiley Interscience: May 19, 2010, XP-002659888.
International Search Report in PCT/EP2011/061443, Oct. 10, 2011.

* cited by examiner (a) $K_{min} = 3$ (b) $K_{min} = 5$ (a) $K_{min} = 3$ (b) $K_{min} = 5$

METHOD AND SYSTEM FOR DISPERSION MEASUREMENTS

FIELD OF THE INVENTION

The invention relates to the field of determining properties of particles in a fluid or gaseous dispersion. More particularly, the present invention relates to the field of determining the concentration of particles in a dispersion.

BACKGROUND OF THE INVENTION

In a variety of applications where nanoscopic particles are involved, such as for example in the field of nanomedicines, virology, nanotoxicology, biosafety, etc., determination of particle concentration in a dispersion is required. Different techniques for determining particle concentration are known.

Some techniques for determining particle concentration in a dispersion make use of microfluidic absorption measurements or fluorescence measurements. The concentration is then determined based on the absorbance properties or fluorescent properties of particles or labels bound to the particles. Another technique used for determining particle concentration is the use of assays. Typically, particles in a dispersion are then specifically bound to labels and the concentration is determined based on the number of labels that can be measured.

Another example for determining particle concentration, whereby no binding of labels to the particles of interest is required, is the use of a Coulter Counter® whereby particles are allowed to flow through a microcapillary of suitable size such that only one particle at a time can reach the measurement region. Particles are detected based on a change in electrical impedance in the liquid filled microchannel. In order to be able to measure such particles, the particles should be larger than 0.4 µm and should have a low electrical conductance.

Analysis of trajectories of dynamic particles using optical microscopy provides a powerful approach to both characterizing particle motion as well as estimating stochastic motion-related parameters, e.g. diffusion coefficient or particle size, and distributions of motion related parameters. Single particle tracking (SPT) is increasingly used as the method of choice to study the behavior of complex systems at small spatial and temporal scales, where traditional ensemble-averaging methods are unable to give a satisfactory account of the complexity of driving processes and function. With the development of tools unhindered in capability by the inherent smoothing effect due to averaging over many particles or over long time lapses, a wealth of information previously beyond reach is now accessible in everyday practice. It is indeed likely that different approaches to the tracking of individual particles or even individual molecules will revolutionize the biophysical and pharmaceutical measurement techniques as these methods become mature and spread. This progress promises to elucidate many aspects of the fundamental interaction of nanomaterials with biological media in the context of nanomedicine, biomedical imaging, medical diagnostics and nanotoxicology. In practice, using image processing, the motion trajectories can be obtained for individual particles that are visible in the SPT movies. Each trajectory can then be analyzed to obtain information on the movement of a particular particle. For example, when particles are undergoing Brownian diffusion, which is e.g. the case for submicron particles in a viscous dispersion, one can estimate the diffusion coefficient of each particle. Since the diffusion coefficient is inversely proportional to the size of the particle, it is possible to perform accurate size measurements of dispersed particles by SPT. Determination of particle concentration in the setting of single particle tracking sometimes is performed by counting the number of particles in an image or the number of particle trajectories that are observed in a given time interval, as e.g. described in Malloy A. and Carr B., Part. Part. Syst. Charact. 23 (2006) 197-204. Converting the observed number of trajectories into a number concentration requires accurate knowledge of the effective volume in which the particles are observed by the SPT instrument. The size of the effective observation volume is typically assumed to be known a priori when the aim is to compute or estimate other physical parameters such as concentration or diffusion coefficient, see for example N. H. Bingham and B. Dunham, "Estimating diffusion coefficients from count data: Einstein-Smoluchowski theory revisited", Ann. Inst. Statist. Math, 49(1997), 667-679. However, it was noted by Malloy and Carr that the effective observation volume depends on the size of the particles and intensity of the light emitted or scattered by the particles. Furthermore, it is clear to a person skilled in the art that the effective observation volume also depends on the signal to noise ratio, background intensity and the image processing settings that are used to detect the particles in the SPT movies. Accurate calibration of the effective detection volume is, therefore, generally not possible by means of a reference measurement using reference particles of known concentration. This is because the actual particles under study and the medium in which they are dispersed might be different from the reference set. Also, the image processing settings may be very different in both cases leading to an altered effective observation volume.

Another shortcoming of SPT concentration measurements based on the number of particle trajectories that was recognized by Malloy and Carr, is that fast moving particles (e.g. small particles) can enter and leave the observation volume more frequently than slow moving particles (e.g. large particles) in the same time interval. Without a suitable correction this will lead to a biased concentration measurement (sampling bias) in that the number of fast moving particles are overestimated compared to more slowly moving particles.

SUMMARY OF THE INVENTION

It is an object of embodiments of the present invention to provide good methods and systems for observing particles in dispersion as well as methods and systems assisting therein. It is an advantage of at least some embodiments of the present invention that good techniques are provided for determining properties of dispersions of particles and/or particles therein based on single particle tracking measurements.

It is an advantage of embodiments according to the present invention that measurement and processing conditions can be inherently taken into account. It is an advantage of embodiments according to the present invention that methods and systems are provided that inherently deal with a sampling bias.

It is an advantage of embodiments according to the present invention, that the effective observation volume can be derived from the time-dependent observations.

It is an advantage of embodiments according to the present invention that accurate values of e.g. the particle concentration can be obtained. It is an advantage of embodiments according to the present invention that accurate values can be obtained based on single particle tracking measurements, even for particles with small diameters such as for example particles having a diameter smaller than 500 nm or smaller than 400 nm.

It is an advantage of embodiments according to the present invention that size distributions can be accurately obtained, not only for a monodisperse set of particles, but also in case of samples that are polydisperse with respect to a motion related parameter.

It is an advantage of embodiments according to the present invention that particle number concentration of particles in dispersion can be accurately determined from the dispersion without a priori knowledge of the effective observation volume, even for particles having a diameter size smaller than 500 nm.

It is an advantage of embodiments according to the present invention that both accurate number concentration of particles in dispersion, even for particles having a characteristic size of 500 nm and/or smaller, can be obtained in combination with size measurements, such that the number concentration as a function of size of the particles can be obtained.

It is an advantage of some embodiments according to the present invention that accurate concentration measurements can be obtained based on single particle tracking measurements. The above objective is accomplished by a method and device according to the present invention.

It is an advantage of some embodiments according to the present invention that accuracy can be further enhanced by taking into account a model whereby the number of particles determined is based on trajectories rather than occurrences of images spots in individual images. The former may be advantageous because identification of particles in a single image can be difficult, sometimes resulting in the occurrence of false hits.

It is an advantage of embodiments of the present invention that the SPT concentration measurements can be performed for particles having a typical or average diameter in the range 10 nm to 1000 nm.

It is an advantage of embodiments of the present invention that the observation volume of the observation technique is inherently taken into account, without the need for a calibration for the observation volume.

The present invention relates to a method for determining a size or shape related parameter of an effective observation volume for an observation technique for particles undergoing at least partially stochastic motion in a dispersion, based on a time-series of observations, the method comprising determining one or more time-dependent characteristics of the dispersion or its particles, based on the time-series of observations, determining at least one stochastic motion-related parameter representative for the at least partially stochastic motion of at least one particle in the dispersion, and determining a size or shape related parameter of the effective observation volume by modeling of the at least partially stochastic motion of the particle movement in the dispersion, the modeling taking into account the at least one stochastic motion-related parameter and the determined one or more time-dependent characteristics. It is an advantage of embodiments according to the present invention that an effective observation volume used in observation techniques for observing particles in dispersion can be determined or taken into account without the need for separately calibrating the effective volume through measurement. It is an advantage of embodiments according to the present invention that an effective observation volume used in observation techniques for observing particles in dispersion can be determined without requiring a calibration experiment. The motion-related parameter may be characteristic for the at least partially stochastic motion. The motion-related parameter may allow for deriving a position, velocity or acceleration of the motion directly based on the motion-related parameter. It may be a parameter deterministic for the motion.

Determining one or more time-dependent characteristics of the dispersion or its particles, based on the time-series of observations, may comprise determining at least a time-dependent characteristic that inherently varies stochastically in time.

The method furthermore may comprise determining the concentration of particles in the dispersion based on the size or shape related parameter of the effective observation volume and the one or more characteristics.

Determining the concentration of particles may comprise determining the concentration as a function of the at least one stochastic motion-related parameter or a parameter derived therefrom.

Determining the concentration of particles may comprise determining the concentration of particles inherently taking into account the effective observation volume in a calibration free manner.

Determining a concentration may comprise determining a concentration distribution as a function of a stochastic motion-related parameter or a parameter derived therefrom, taking into account the stochastic motion-related parameter so as to compensate for the mobility dependent probability that an individual particle is present in the effective observation volume.

Determining one or more time-dependent characteristics may comprise determining from the time-series of observations trajectories for individual particles in the dispersion, and determining the distribution of number of trajectories versus particle trajectory length, wherein determining a size or shape related parameter of the effective observation volume may comprises modeling the at least partially stochastic motion of the particle movement in the dispersion based on the at least one stochastic motion-related parameter and the trajectory length distribution.

The at least one stochastic motion-related parameter may be determined from the trajectory of at least one particle.

The method furthermore may comprise determining the concentration of particles in the dispersion based on the number of trajectories and the size or shape related parameter of the effective observation volume.

Determining one or more characteristics may comprise determining a number of particles in observation in at least two different points in time.

The method may comprise determining the number concentration of particles in the dispersion based on the number of particles in observation and the effective observation volume.

Modeling of the at least partially stochastic motion of the particle movement in the dispersion may comprise modeling the stochastic process describing the number of observed particles in each frame.

The present invention also relates to a system for determining a size or shape related parameter of an effective observation volume for an observation technique for particles undergoing at least partially stochastic motion in a dispersion based on a time-series of observations, the system comprising an input means for receiving one or more time-dependent characteristics of the dispersion or its particles based on the time-series of observations, a processing means for determining at least one stochastic motion-related parameter representative for the at least partially stochastic motion of at least one particle in the dispersion and for determining a size or shape related parameter of the effective observation volume by modeling of the at least partially stochastic motion of the particle movement in the dispersion, the modeling taking into account the at least one stochastic motion-related parameter and the determined one or more time-dependent characteristics.

The processing means may be adapted for determining the concentration of particles in the dispersion based on a size or shape related parameter of the effective observation volume and the one or more time-dependent characteristics.

The processing means may be adapted for determining the concentration as a function of the at least one stochastic motion-related parameter or a parameter derived therefrom.

The processing means may be adapted for determining a concentration distribution as a function of a stochastic motion-related parameter or a parameter derived therefrom, taking into account the stochastic motion-related parameter so as to compensate for the mobility dependent probability that an individual particle is present in the effective observation volume.

The processing means may be adapted for determining from the time-series of observations trajectories for individual particles in the dispersion, and for determining the distribution of number of trajectories versus particle trajectory length and wherein the processing means is adapted for modeling of the at least partially stochastic motion of the particle movement in the dispersion, the modeling taking into account at least one stochastic motion-related parameter and the trajectory length distribution for determining the size or shape related parameter of the effective observation volume.

The processing means may be adapted for determining the at least one stochastic motion-related parameter from the trajectory of at least one particle.

The processing means furthermore may be adapted for determining the concentration of particles in the dispersion based on the number of trajectories and the size or shape related parameter of the effective observation volume.

The processing means may be adapted for determining one or more characteristics by determining a number of particles in the effective observation volume in at least two different points in time.

The processing means may be adapted for determining a number of particles in observation in at least two different points in time, the particles in the observations in at least two different points in time being not the same.

The processing means may be adapted for determining the concentration of particles in the dispersion based on the number of particles in observation and the size or shape related parameter of the effective observation volume.

The system with the processing means may be adapted for determining a diffusion coefficient.

The processing means may be adapted for applying a model based on a Gaussian random walk.

The system may be implemented as a computer program product for, when executing on a computer, performing a method for determining a concentration of nanoparticles in a dispersion.

The input means may comprise an optical inspection system for determining a plurality of single particle trajectories.

The present invention also relates to a data carrier comprising a set of instructions for, when executed on a computer, performing a method for determining a size or shape related parameter of an effective observation volume for an observation technique for particles undergoing at least partially stochastic motion in a dispersion, the method comprising determining one or more time-dependent characteristics of the dispersion or its particles based on a time-series of observations, determining at least one stochastic motion-related parameter representative for at least partially stochastic motion of at least one particle in the dispersion and determining a size or shape related parameter of the effective observation volume by modeling of the at least partially stochastic motion of the particle movement in the dispersion, the modeling taking into account the at least one stochastic motion-related parameter and the determined one or more time-dependent characteristics.

The data carrier may be any of a CD-ROM, a DVD, a flexible disk or floppy disk, a tape, a memory chip, a processor or a computer.

The present invention also relates to a computer program product for performing, when executed on a computer, a method as described above, as well as the transmission of such a computer program product over a network and/or a data carrier comprising such a computer program product.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
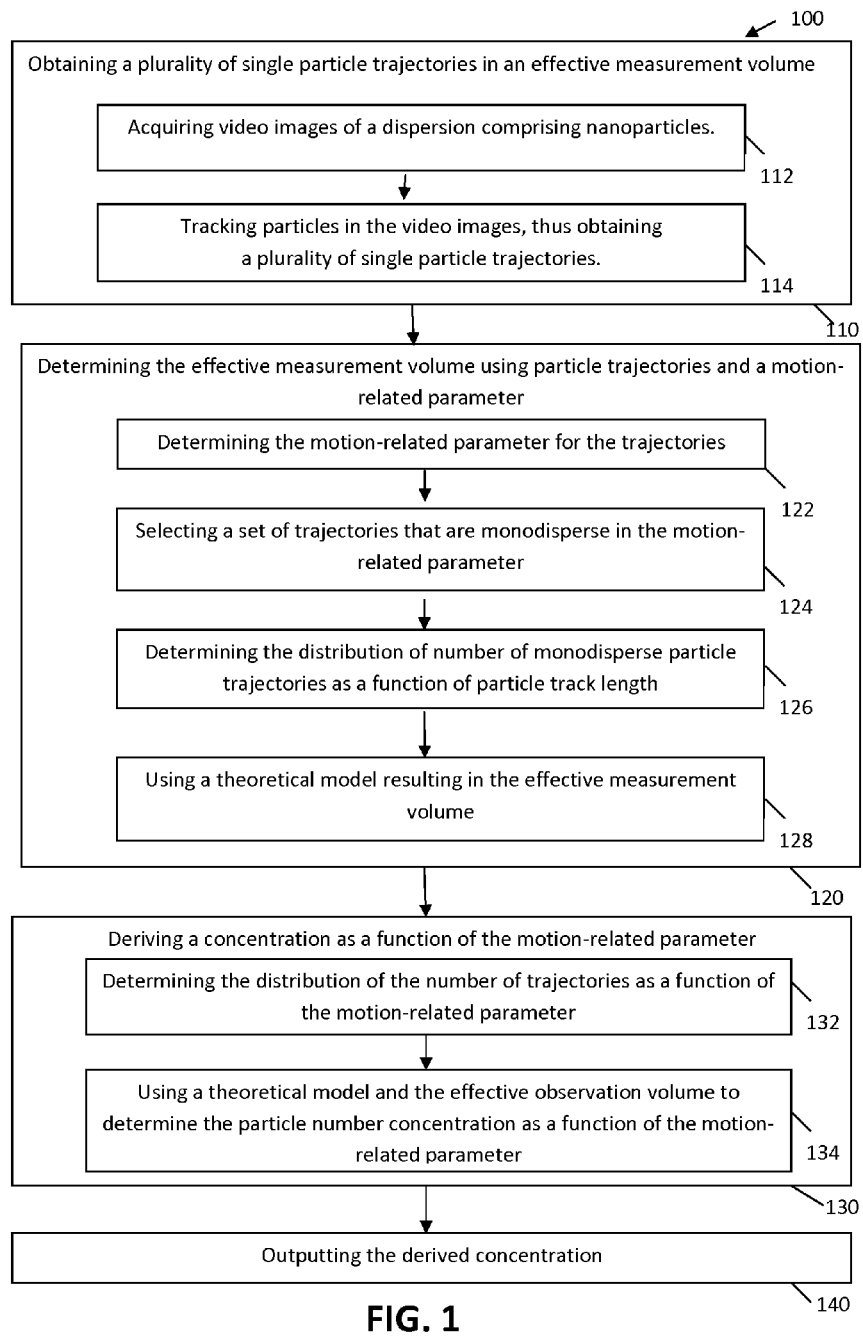
FIG. 1 illustrates an overview of an exemplary method for determining an effective observation volume and optionally for determining a number concentration of particles in a dispersion, according to an embodiment of the present invention.

Any reference signs in the claims shall not be construed as limiting the scope. In the different drawings, the same reference signs refer to the same or analogous elements.

DETAILED DESCRIPTION OF ILLUSTRATIVE EMBODIMENTS

Embodiments of the invention now will be illustrated and described in detail in the drawings and foregoing description, but such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures will be recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The following description details certain embodiments of the invention. It will be appreciated, however, that no matter how detailed the following appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

Where in embodiments of the present invention reference is made to monodisperse, reference is made to a parameter having a small range of values, typically with a coefficient of variation of less than 5% or less than 10%, although embodiments of the present invention are not limited thereto. Where in embodiments of the present invention reference is made to diffusive motion, reference is made to any kind of partially or completely stochastic motion exhibited by particles in suspension dispersion, including but not limited to Brownian motion (also denoted as free diffusion), free diffusion with drift (nonzero deterministic component), simple random walk, Gaussian random walk, subdiffusive motion, superdiffusive motion, fractional diffusive motion, hindered diffusion, including all combinations of such motion and approximations thereof, representations and theoretical models for such motion including approximations thereof, in continuous and/or discrete time, and in continuous and/or discrete space, including mutually independent and/or mutually dependent particles, the latter with any model of interaction, and including any boundary conditions at the boundaries of the suspension dispersion.

Where in embodiments of the present invention reference is made to particle, reference is made to any type of physical and/or simulated particle exhibiting at least partially stochastic motion, regardless of size, shape, charge or other physical properties unless otherwise explicitly stated. Such particles typically may have a characteristic diameter in the range 1 nm to 10 µm.

Where in embodiments of the present invention reference is made to nanoparticles or nanosized particles, reference is made to particles having a characteristic diameter, e.g. an average diameter, between 1 nm and 1 µm, e.g. between 10 nm and 1000 nm or between 10 nm and 500 nm.

Where in embodiments of the present invention reference is made to particles in a dispersion or dispersed particles, reference is made to particles, molecules, atoms, subatomic particles or combinations thereof that are dispersed throughout a gaseous, liquid, solid or semi-solid medium.

Where in embodiments according to the present invention reference is made to characteristic size or typical size, reference is made to an average diameter of the object. Where in embodiments of the present invention reference is made to a characteristic diameter, reference is made to an average diameter of the object. Where reference is made to an average diameter of an object, reference may be made to the diameter of a corresponding sphere having the same volume as the object under study.

Where in embodiments of the present invention reference is made to a track or a trajectory, reference is made to the path a particle travels in a dispersion in which particles are performing diffusive motion, or alternatively, reference is made to a set of time-discrete sampled points of such a path.

Where in embodiments of the present invention reference is made to an observation volume or effective observation volume, reference is made to a space, region or volume or geometric object, comprising a part of a suspension or dispersion, in which particles exhibiting diffusive motion can be detected and/or tracked through time by means of a detection technique, such as using an imaging device and particle tracking device, or approximations of such a volume or geometric object. The effective observation volume thus is not only determined by the optical volume that is in focus, but also may be affected by the video acquisition or processing and/or the tracking algorithm. An effective size of the observation volume may be for example a diameter in one direction of the observation volume, a characteristic area, the observation volume itself, etc.

Where in embodiments of the present invention reference is made to a parameter of the observation volume or effective observation volume, reference may be made to a characteristic size, to a shape, etc. of the observation volume. Where reference is made to the size of an observation volume or effective observation volume, reference is made to the volumetric size of the corresponding geometric object, the size of characteristic subdimensions of the volume or approximations thereof.

Where in embodiments of the present invention reference is made to a trajectory length, reference is made to the number of consecutive (in time) frames of a time-lapse image sequence in which an individual particle appears inside a thereto related observation volume or effective observation volume.

Where in embodiments of the present invention reference is made to a trajectory length distribution, reference is made to a probability distribution of occurrence of trajectories inside an effective observation volume as a function of trajectory length. A trajectory length distribution is a function of a stochastic motion-related parameter and an effective observation volume.

Where in embodiments of the present invention reference is made to a stochastic motion-related parameter, reference is made to any parameter that can be used to describe the diffusive motion in terms of its motility, mobility, average velocity, velocity distribution, or distribution of spatial increments.

Where in embodiments of the present invention reference is made to a concentration, reference is made to a measure of how much substance per unit of volume is mixed with another substance or a concentration measure derived therefrom, such as but not limiting to the mass concentration, the volume concentration and the number concentration.

Where in embodiments of the present invention reference is made to a number concentration, reference is made to the number of particles residing per unit of volume or to the average number of particles over time residing per unit of volume.

In a first aspect, the present invention relates to a method for determining a size or shape related parameter of an effective observation volume for an observation technique for particles undergoing at least partially stochastic motion in a dispersion. The technique is based on a time-series of observations. The method may be applied in a method for determining a concentration of particles in a dispersion, although embodiments of the present invention are not limited thereto. The method according to embodiments of the present invention comprises determining one or more time-dependent characteristics of the dispersion or of its particles based on the time-series of observations. Determining one or more time-dependent characteristics may for example be determining one or more single particle trajectories in the observation volume. In another example determining one or more time-dependent characteristics may be determining the number of particles visible in different observations of the observation volume or the fluctuation thereof. The method also comprises determining at least one stochastic motion-related parameter representative for the at least partially stochastic motion of at least one particle in the dispersion and determining a size or shape related parameter of the effective observation volume by modeling of the at least partially stochastic motion of the particle movement in the dispersion, the modeling taking into account the at least one stochastic motion-related parameter and the determined one or more time-dependent characteristics. In one set of embodiments, the method is based on time-lapse imaging and derivation of single particle motion trajectories from the image time-series. In this way, a plurality of single particle trajectories in an effective observation volume is obtained.

One or more single particle trajectories can be obtained. Advantageously several tens, hundreds or more single particle trajectories are used. Obtaining the plurality of single particle trajectories may comprise determining the plurality of single particle trajectories e.g. experimentally, or it may comprise receiving a plurality of single particle trajectories as data previously recorded or stored. The latter can be performed using any suitable single particle tracking means. Embodiments of the present invention also comprise determining a motion related parameter and determining a size or shape related parameter of the effective observation volume making use of a theoretical model that is based on the relation between at least one stochastic motion-related parameter of the individual trajectories, the trajectory length distribution and the effective observation volume. The theoretical model thus advantageously allows for an inherent calibration of the effective observation volume from the single particle trajectory data. Some embodiments of the present invention also may comprise deriving a concentration of particles taking into account the number of detected particle trajectories and the effective observation volume. In some embodiments the method comprises determining particle concentration as function of the motion parameter or a parameter derivable therefrom using a theoretical model based on the number of detected particle trajectories, the effective observation volume, and at least one stochastic motion-related parameter. For example, the method may provide determining particle concentration as function of the diffusion coefficient or determining particle concentration as function of the particle size. In another set of embodiments, the method comprises determining the number of particles in the observation volume in at least two observations made at a different moment in time, obtaining a stochastic motion-related parameter and determining a parameter for the effective observation volume based on a theoretical model taking into consideration the stochastic motion-related parameter and the information related to the time-dependent number of particles in the observation volume.

By way of illustration, embodiments of the present invention not being limited thereto, an exemplary first method according to an embodiment of the present invention is further discussed below and with reference to FIG. 1. The method 100 for determining a size or shape related parameter of an effective observation volume and optionally also the particle number concentration of nanoparticles in a dispersion illustrates standard and optional steps.

Figure 2:
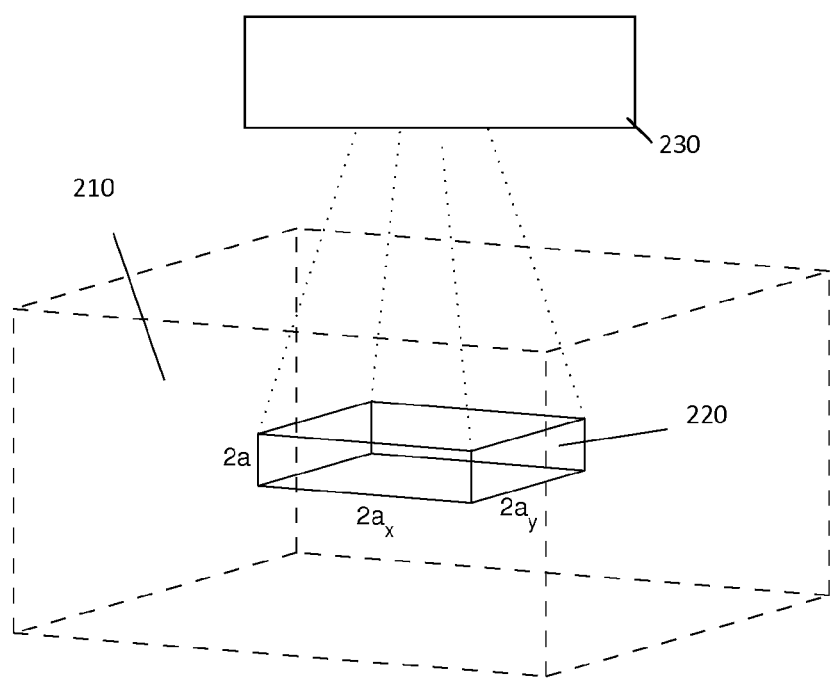
FIG. 2 illustrates an example of an effective observation volume as is used in an embodiment according to the present invention.

In a first step 110, the method 100 comprises obtaining a plurality of single particle trajectories in an effective observation volume. Obtaining such a plurality of single particle trajectories may be receiving the data via a data input channel or may be determining a plurality of single particle trajectories, e.g. through measurement. The method may comprise acquiring video images 112 of a dispersion comprising nanoparticles and tracking particles 114 in the video images, thus obtaining a plurality of single particle trajectories. Acquiring video images 112 may comprise irradiating a dispersion of particles and capturing a plurality of images in a time sequence such that a dynamic view of the imaged volume of the dispersion is obtained. By way of illustration, FIG. 2 illustrates an example of a dispersion 210, the effective observation volume 220, an optical detection system 230, such as for example a microscope setup, whereby the effective observation volume 220 may be determined by the irradiation and/or focusing condition, the image acquisition and/or the particle tracking procedure. In such an experimental setup, the field of view may constitute a rectangular box approximately centered in the liquid dispersion. Typically, particles outside the field of view cannot be tracked. Tracking may be performed using a nearest neighbor algorithm or more complex algorithms known to a person skilled in the art that additionally make use of other particle properties, such as shape, intensity, history of movement etc.

In a further step 120, the method comprises determining a size and/or shape related parameter of the effective observation volume making use of a theoretical model based on the particle trajectories and at least one stochastic motion-related parameter for the motion trajectories. Conveniently, the at least one stochastic motion-related parameter may be derived from the motion trajectories using theoretical considerations. By selecting a subset of trajectories that are monodisperse in the at least one stochastic motion-related parameter, the effective observation volume can be determined from their trajectory length distribution using the theoretical model. The stochastic motion-related parameter may be for example a diffusion coefficient. An example of a model by which an effective size of a observation volume can be derived, is discussed by way of example below, embodiments of the present invention not being limited thereto. The model in one example may be a model based on a Gaussian random walk. The model alternatively may be any model exactly or approximately describing diffusive motion of particles in dispersion. In one example, determining the effective observation volume 120 may comprise the steps of determining a stochastic motion-related parameter, e.g. diffusion coefficient, for each trajectory 122, selecting a set of trajectories that are monodisperse in the stochastic motion-related parameter 124, determining the trajectory length distribution 126 of the subset of trajectories that are monodisperse in the diffusion coefficient, and using a model 128 resulting in a parameter of the effective observation volume, e.g. a size of the effective observation volume.

In an optional further step 130, the method comprises deriving a concentration taking into account the effective observation volume. By way of example, embodiments of the present invention not being limited thereto, deriving a concentration may comprise determining a concentration using a length distribution of the particle trajectories and the motion related parameter. The concentration may be determined as function of the stochastic motion-related parameter or a parameter derivable therefrom. In one particular embodiment, deriving a concentration 130 comprises determining the distribution of the number of trajectories as a function of the stochastic motion-related parameter 132 and using a theoretical model and the effective observation volume for determining the particle number concentration as a function of the stochastic motion-related parameter.

In an optional further step 140, the method comprises outputting the derived concentration, e.g. by displaying it, outputting data via an output channel, etc.

The method according to embodiments of the present invention may be an automated and or automatic method. The method may be a computer implemented method and may be implemented software-matic or hardware-matic. The method furthermore may comprise further optional steps, as known by the person skilled in the art, such as for example filtering, thresholding, etc.

Figure 3:
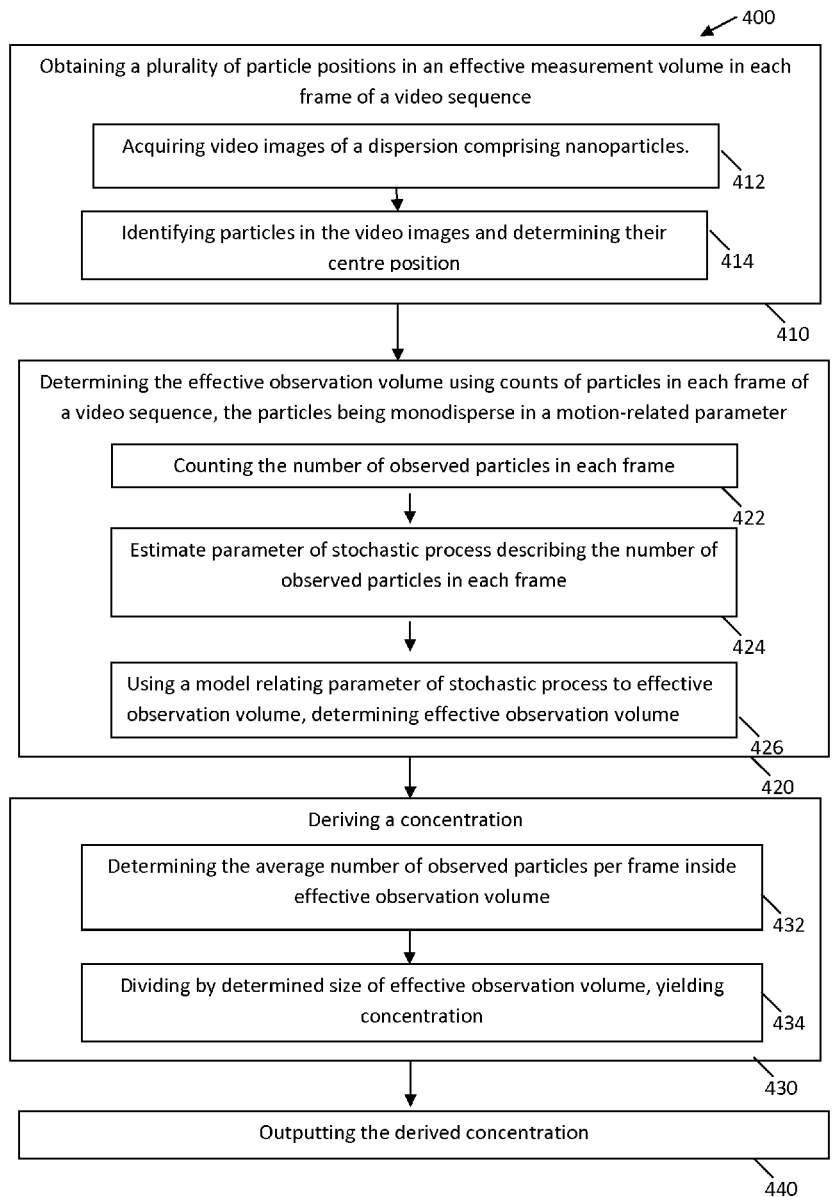
FIG. 3 illustrates an overview of an exemplary method for determining an effective observation volume and optionally for determining number concentration of particles in a dispersion, according to an embodiment of the present invention.

By way of illustration, embodiments of the present invention not being limited thereto, an exemplary second method according to an embodiment of the present invention is further discussed below and with reference to FIG. 3. The method 400 for determining a size or shape related parameter of the effective observation volume and optionally also for determining particle concentration of nanoparticles in a dispersion illustrates standard and optional steps.

In a first step 410, the method 400 comprises determining the number of particles detected in an effective observation volume as determined for at least two points in time of a time-series of observations. Preferably, the number of particles within the observation volume is determined for a plurality of points in time, such as but not limiting to 10, 100 or more. In one example, the time-series of observations may be a sequence of frames in a video sequence. Obtaining such particle numbers may be receiving the data via a data input channel or may be determining the number of particles through measurement. In one specific example, the method may comprise acquiring video images 412 of a dispersion comprising nanoparticles and identifying particles 414 in the video images, thus obtaining the number of particles in each frame of the video sequence. Acquiring video images 412 may comprise irradiating a dispersion of particles and capturing a plurality of images in a time sequence such that a dynamic view of the imaged volume of the dispersion is obtained. As indicated above, an example of an effective observation volume 220 is shown in FIG. 2 and may depend on the irradiation and/or focusing condition, the image acquisition and/or the particle identification procedure. In such an experimental setup, the effective observation volume may constitute a rectangular box approximately centered in the liquid dispersion. Particles outside the effective observation volume cannot be identified. Particle detection may be performed using image processing algorithms as are known to a person skilled in the art.

The exemplary method also comprises determining a size or shape related parameter of the effective observation volume 420 using counts of particles in the set of observations performed at different points in time. The exemplary method may comprise counting 422 the number of particles, observed in step 410. The exemplary method also comprises determining a stochastic process from a parametrized family of such, by means of statistical estimation of its parameters from the particle count data, the stochastic process exactly or approximately describing the particle count data as indicated in step 424, and subsequently using a model 426 adapted for relating an estimate of the parameter of such a stochastic process to the effective observation volume, hence determining the effective observation volume. An example of how to determine the effective observation volume from such particle count data is discussed by way of example below, embodiments of the present invention not being limited thereto.

In a further optional step 430, the method comprises deriving a concentration. By way of example, embodiments of the present invention not being limited thereto, concentration may be determined by 432 determining the average number of observed particles per frame inside effective observation volume, and 434 dividing by determined size of effective observation volume, yielding concentration.

In an optional further step 440, the method comprises outputting the derived concentration, e.g. by displaying it, outputting data via an output channel, etc.

The method according to embodiments of the present invention may be an automated and or automatic method. The method may be a computer implemented method and may be implemented software-matic or hardware-matic. The method furthermore may comprise further optional steps, as known by the person skilled in the art, such as for example filtering, thresholding, analyzing uncertainty of determination of effective observation volume and subsequently concentration, thereby obtaining confidence intervals, etc.

Figure 4:
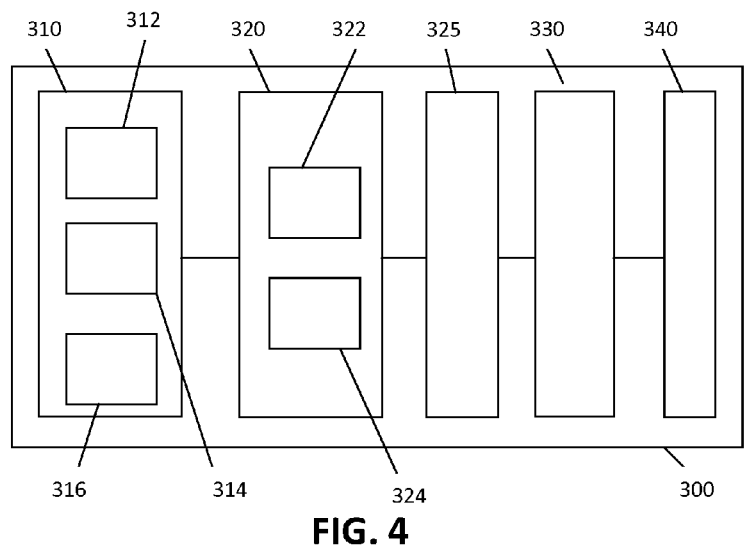
FIG. 4 illustrates an exemplary system for determining particle concentration of nanoparticles in a dispersion, according to an embodiment of the present invention.

In a second aspect, the present invention relates to a system for determining a size or shape related parameter of the effective observation volume or for furthermore determining a concentration of nanoparticles undergoing at least partially stochastic motion in a dispersion, based on an a time-series of observations. In some embodiments, the method may be applied for a single particle tracking observation technique. The system according to embodiments of the present invention comprises an input means for receiving one or more time-dependent characteristics of the dispersion or its particles based on the time-series of observations, and a processing means for determining a stochastic motion-related parameter representative for the at least partially stochastic motion of at least one particle in the dispersion and for determining a size or shape related parameter of the effective observation volume by modeling of the at least partially stochastic motion of the particle movement in the dispersion, the modeling taking into account the at least one stochastic motion-related parameter and the determined one or more time-dependent characteristics. By way of illustration, embodiments of the present invention not being limited thereto, an exemplary system 300 is shown in FIG. 4. The system 300 for determining nanoparticle concentration comprises an input means 310 for obtaining a plurality of single particle trajectories. The input means may comprise an input port or, for example in one embodiment, may comprise an irradiation source 312, an image capturing means 314 such as for example a CCD camera and a particle tracking means 316 for tracking single particle trajectories in the video sequence. Alternatively, the input means may be adapted for recording the number of particles in an observation volume for a time-series of observations. Advantageously a system is used that is suitable for detection of particles. The imaging system typically may comprise a sensitive camera, such as for example a CCD camera. Furthermore the imaging system may comprise an illumination system adapted for providing illumination of a dispersion in a region of interest. The illumination system may comprise a radiation source and a focusing system. The focusing system advantageously may assist in providing illumination of the region of interest while having little or no contribution of background radiation from out of focus regions. The system furthermore comprises a processing means 320 for determining a stochastic motion-related parameter. In some embodiments this may be based on the single particle trajectories. Alternatively, this may be based on the number of particles in the observation volume for a plurality of observations made at different times. The processing means 320 in one embodiment may comprise a diffusion coefficient determinator 322, a distribution determinator 324 for determining the distribution of the number of particle trajectories as function of the particle length. The system furthermore comprises a processor 325 for determining a size or shape related parameter of the effective observation volume by modeling of the at least partially stochastic motion of the particle movement in the dispersion, the modeling taking into account the at least one stochastic motion-related parameter and the determined one or more time-dependent characteristics. The system furthermore optionally may comprise a concentration deriving processor 330 for deriving a concentration taking into account the stochastic motion-related parameter and the effective observation volume. The latter may be adapted for determining a concentration using the length of the particle trajectories and the motion related parameter as well as the size or shape related parameter of the effective observation volume. Alternatively, the concentration deriving processor may be adapted for deriving a concentration taking into account the number of particles determined and the size or shape related parameter of the effective observation volume determined. The concentration deriving processor furthermore may be adapted for determining a concentration as function of the stochastic motion-related parameter or as function of a parameter derivable therefrom. The system furthermore may comprise an output means 340 for outputting the processed results, such as for example an output port or a display or memory or alike. Further components also may be present, such components expressing one or more functionalities of steps as described in a method according to the first aspect or such components being optional components also typically present in particle tracking systems known from prior art. The system may be a processing system, performing only the processing of the single particle trajectory data. Alternatively the system also comprises irradiation and acquisition components. Different processors or processing components described above may be grouped in a single processor providing the different functionalities, although embodiments are not limited thereto.

Figure 5:
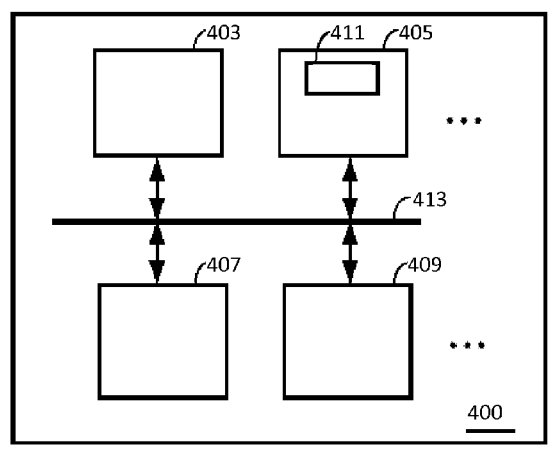
FIG. 5 illustrates an exemplary processing system as can be used for implementing a method according to an embodiment of the present invention.

In yet another aspect, the present invention relates to a processing system or processor wherein the method or system for determining a size or shape related parameter for the effective observation volume and optionally for determining a particle concentration as described in embodiments of the previous aspects are implemented in a software based manner. FIG. 5 shows one configuration of a processing system 400 that includes at least one programmable processor 403 coupled to a memory subsystem 405 that includes at least one form of memory, e.g., RAM, ROM, and so forth. It is to be noted that the processor 403 or processors may be a general purpose, or a special purpose processor, and may be for inclusion in a device, e.g., a chip that has other components that perform other functions. Thus, one or more aspects of embodiments of the present invention can be implemented in digital electronic circuitry, or in computer hardware, firmware, software, or in combinations of them. The processing system may include a storage subsystem 407 that has at least one disk drive and/or CD-ROM drive and/or DVD drive. In some implementations, a display system, a keyboard, and a pointing device may be included as part of a user interface subsystem 409 to provide for a user to manually input information. Ports for inputting and outputting data also may be included. More elements such as network connections, interfaces to various devices, and so forth, may be included, but are not illustrated in FIG. 5. The various elements of the processing system 400 may be coupled in various ways, including via a bus subsystem 413 shown in FIG. 5 for simplicity as a single bus, but will be understood to those in the art to include a system of at least one bus. The memory of the memory subsystem 405 may at some time hold part or all (in either case shown as 411) of a set of instructions that when executed on the processing system 400 implement the steps of the method embodiments described herein. More particularly, the memory may comprise instructions for determining particle concentration of particles in a dispersion etc. Thus, while a processing system 400 such as shown in FIG. 5 as such is prior art, a system that includes the instructions to implement aspects of the methods for determining particle concentration is not prior art, and therefore FIG. 5 is not labeled as prior art. The processor according to embodiments of the present invention may be implemented to existing particle observation systems such as for example in particle tracking systems.

The present invention also includes a computer program product which provides the functionality of any of the methods according to the present invention when executed on a computing device. Such computer program product can be tangibly embodied in a carrier medium carrying machine-readable code for execution by a programmable processor. The present invention thus relates to a carrier medium carrying a computer program product that, when executed on computing means, provides instructions for determining particle concentration according to any of the methods as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

Without embodiments of the present invention being limited thereby, the principle of at least some embodiments of the present invention is based on the understanding that the number of observed particle trajectories must be proportional to the concentration of the particles in the dispersion, but whereby a sampling bias effect introduced due to the fact that particles are only visible when entering the effective observation volume, that may e.g. be determined at least partially by the focal plane of the microscope. As a result small and fast moving particles will appear frequently in and out of the focal plane and will give rise to many short trajectories, i.e. trajectories covering a short period in time and consisting of few detected particle positions. Large and slowly moving particles, on the other hand, will produce fewer but longer trajectories, i.e. trajectories covering a longer period in time and consisting of more detected particle positions. It furthermore has been surprisingly found that a technique can be developed whereby the effective observation volume, also determining whether particles can be seen or not, can be taken into account automatically.

Figure 6:
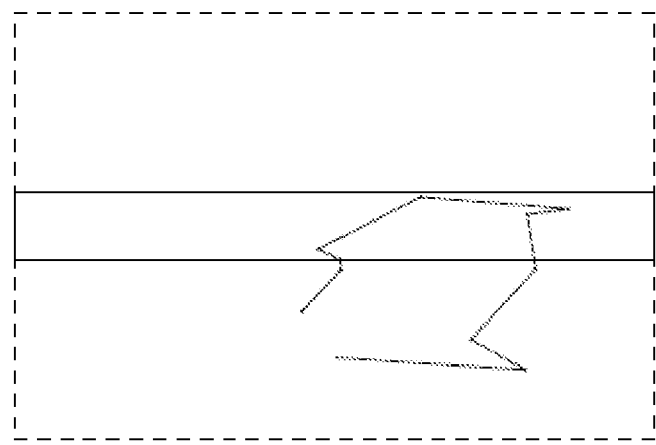
FIG. 6 illustrates an example of a particle trajectory which can assist in determining a concentration, according to an embodiment of the present invention.

By way of illustration, embodiments of the present invention not being limited thereto, a model of an exemplary method according to an embodiment of the present invention is described below. Embodiments of the present invention are also not limited to or restricted by the mathematical formalism used for illustrating. In the present illustration, an example of a modeling of the distribution of the observed trajectory lengths as function of the diffusion coefficient is provided. The model in the present example takes into account the tracking depth (the distance from the nearest trackable particle to the most distant trackable particle, i.e. the axial dimension of the observation volume), the time lapse and the thickness of the liquid dispersion. A simplification will be introduced by assuming that particles are entering and exiting the observation volume only by means of axial diffusion, i.e. parallel to the optical axis. The three-dimensional system is hence replaced by a one-dimensional model (see FIG. 6). Assume that particles diffuse back and forth within $[-A,A]$, are in focus within $[-a,a]$, and out of focus otherwise. Hence, the thickness of the liquid dispersion is $2A$ and the tracking depth is $2a$. Assume that A is much larger than a. The assumption that the field view is centered in the liquid dispersion is not crucial, but provides for symmetry in computations. What is crucial, however, is that the distance from the observation volume to the nearest boundary of the dispersion is much larger than a.

A Gaussian random walk model for computing the trajectory length distribution is employed. The model will, in lack of an analytical solution, be based on successive numerical convolutions as described below.

Let $\phi$ be the standard normal density and $\Phi$ be the standard normal cumulative distribution function, i.e.

$$\phi(z) = \frac{1}{\sqrt{2\pi}} e^{-\frac{1}{2}z^2} \qquad [1]$$

and $$\Phi(z) = \int_{-\infty}^{z} \phi(t)\,dt \qquad [2]$$

Because of thermodynamic equilibrium, it can be assumed that the particles are uniformly distributed over $[-A,A]$. Hence, all particles out of focus are uniformly distributed over $[-A,-a] \cup [a,A]$. All these particles' positions in the next time step will be their previous position plus a Gaussian increment. Since the probability density of the sum of two independent random variables is the convolution of the two variables' probability densities, the distribution of particles in the next time step can be expressed as a convolution. The probability density of a particle that has just entered the observation volume is $$f_1(z) = \begin{cases} \frac{h(z)}{\int_{-a}^{a} h(z)\,dz}, & z \in [-a, a] \\ 0, & z \notin [-a, a] \end{cases} \qquad [3]$$

where $$h(z) = \frac{1}{2(A-a)}\left(\Phi\left(\frac{z+A}{\sqrt{2D\Delta t}}\right) - \Phi\left(\frac{z+a}{\sqrt{2D\Delta t}}\right) + \Phi\left(\frac{z-a}{\sqrt{2D\Delta t}}\right) - \Phi\left(\frac{z-A}{\sqrt{2D\Delta t}}\right)\right) \qquad [4]$$

and D is the diffusion coefficient. Given the initial distribution of particles that have just entered the observation volume, distributions in the subsequent time steps can be acquired by successive convolutions. Let $Z_k$, $k \geq 1$, denote the kth spatial (axial) position of a particle and let the trajectory length K be the largest integer K such that $-a \leq Z_k \leq a$ for $1 \leq k \leq K$. Define $$f_k(z) = \frac{d}{dz} P(Z_k \leq z, K \geq k) \geq .$$

Then the density in the next time step can be written as a convolution with a Gaussian, $$f_k(z) = \int_{-\infty}^{\infty} f_{k-1}(x) G(z-x)\,dx, z \in [-a,a] \qquad [5]$$

and $f_k(z)=0$, $z \notin [-a,a]$ where G is the Gaussian propagator $$G(z) = \frac{1}{\sqrt{2D\Delta t}} \phi\left(\frac{z}{\sqrt{2D\Delta t}}\right) \qquad [6]$$

Thus the densities $f_k, k \geq 1$ can be recursively computed numerically. The computations can be made considerably faster by use of expansion in a space of equidistant translates $\{\psi_1, \ldots, \psi_n\}$ of a Gaussian kernel, $$\psi_i(z) = \left(\frac{1}{w}\right)\phi\left(\frac{z-m_i}{w}\right).$$

Further it is found that $$P(K \geq k) = \int_{-a}^{a} f_k(z) dz. \quad [7]$$

The probability of a particle uniformly distributed over $[-A,-a]\cup[a,A]$, to enter the field of view is the integral of $h(x)$ over $[-a,a]$, which for diffusion coefficient D equals $$P_{enter}(D) = \frac{1}{A-a} \quad [8]$$

$$\left((A+a)\Phi\left(\frac{A+a}{\sqrt{2D\Delta t}}\right) - (A-a)\Phi\left(\frac{A-a}{\sqrt{2D\Delta t}}\right) - 2aA\Phi\left(\frac{2a}{\sqrt{2D\Delta t}}\right)\right) +$$

$$\frac{\sqrt{2D\Delta t}}{A-a}\left(\phi\left(\frac{A+a}{\sqrt{2D\Delta t}}\right) - \phi\left(\frac{A-a}{\sqrt{2D\Delta t}}\right) - \phi\left(\frac{2a}{\sqrt{2D\Delta t}}\right) + \phi(0)\right)$$

Since the distribution of particles not in focus is the same throughout, the probability that a particle enters the observation volume is not time-dependent. The observed number of particles is proportional to this probability, the concentration of particles, and the duration of video sequence acquisition. The relative sizes of these probabilities determine the relative numbers of particles observed for different diffusion coefficients, so it can be used to model the observed distribution of diffusion coefficients given the true one. In practice, one does not observe every particle that comes into focus; one has a lower threshold on the number of increments due to limitations in the tracking algorithm. If the minimum trajectory length is $K_{min}$, then the probability of observing a particle is $$P_{observe}(D) = P_{enter}(D)P(K \geq K_{min}) \quad [9]$$

Figure 7:
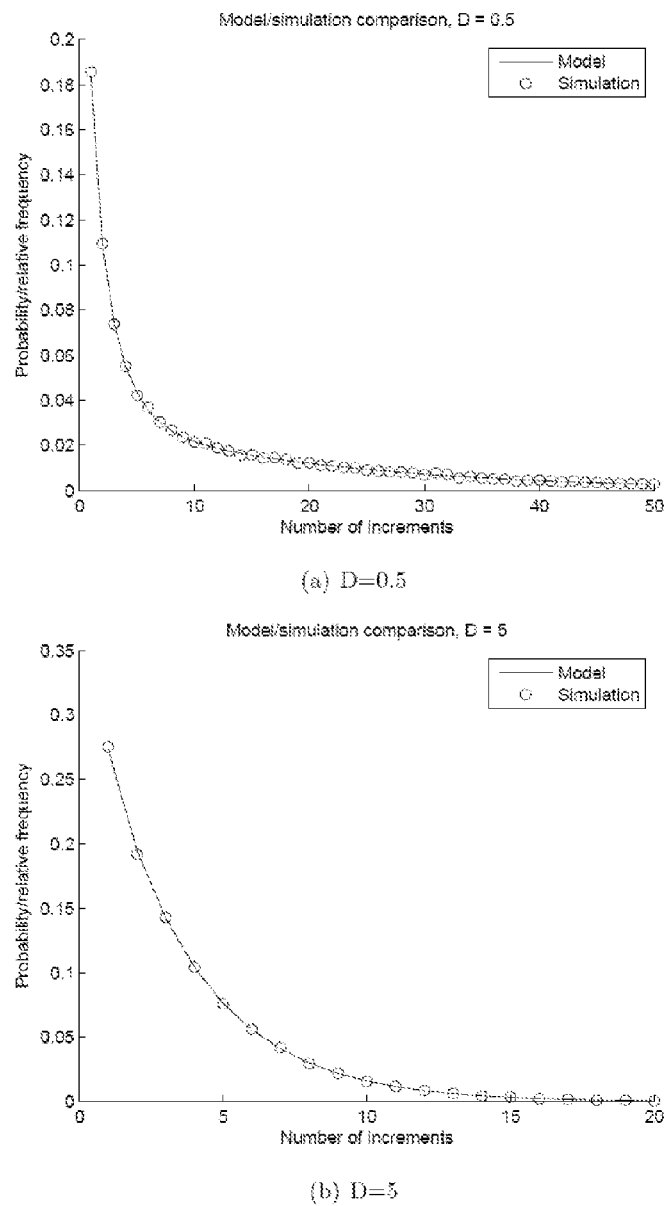
FIG. 7 illustrates a comparison of model probabilities for different K values versus empirical relative frequencies acquired by simulation for different number of increments for $D=0.5$ $\mu m^2/s$ and $D=5$ $\mu m^2/s$, illustrating features of an embodiment of the present invention.

The validity of the model is verified against simulations with $A=60$ μm, $a=0.65$ μm, $\Delta t=21.6$ ms and D equal to 0.5 and 5 μm²/s, respectively. Notice that the trend goes toward shorter trajectories for larger diffusion coefficients and vice versa (see FIG. 7).

Figure 8:
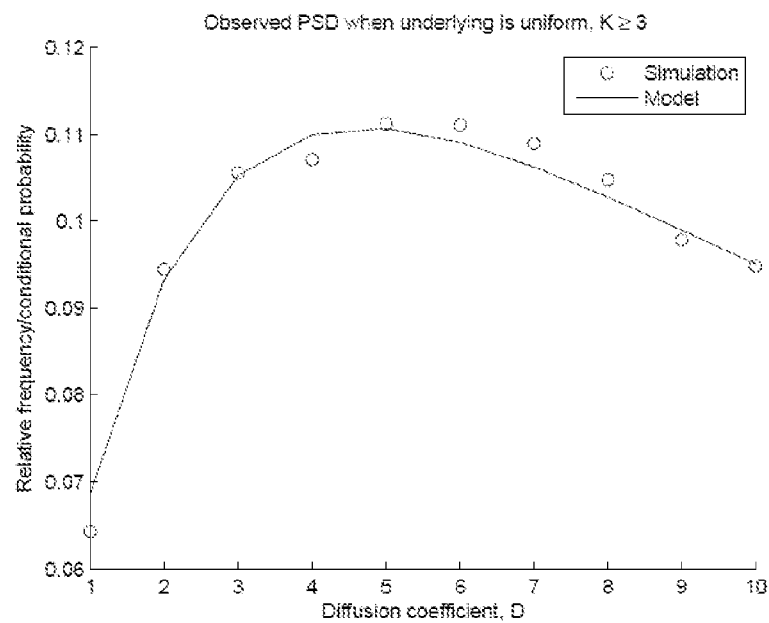
FIG. 8 shows a comparison of model probabilities vs empirical relative frequencies acquired by simulation of the diffusion coefficients or particle sizes, for different lower thresholds on the number of increments, illustrating features of an embodiment of the present invention.
Figure 8:
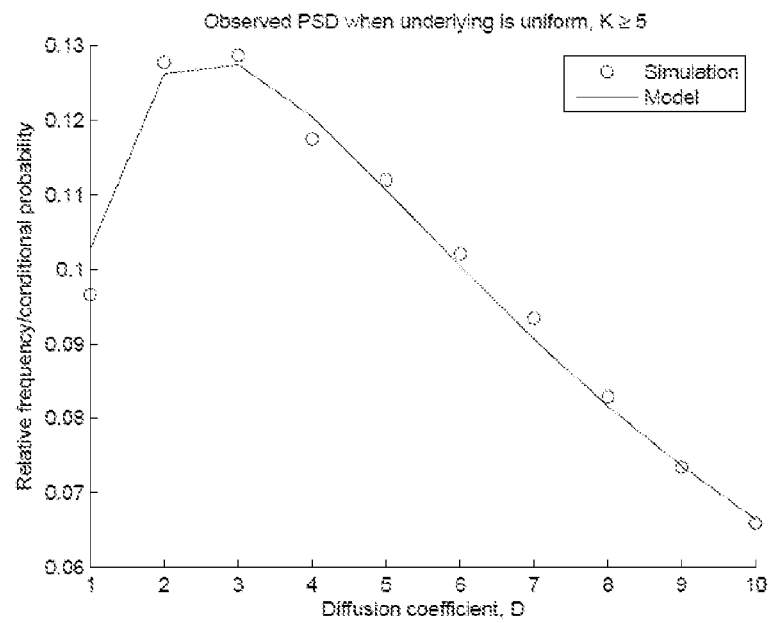

If one has a uniform distribution of particles over some number of diffusion coefficients, the observed distribution of particles will not be uniform due to this size bias. One can correctly estimate this transformation of the distribution by modeling the relative frequency of observed particles by (a normalized version of) the above probability $P_{enter}(D)$. This is illustrated by simulation, considering the cases $K_{min}=3$ and $K_{min}=5$ and comparing simulation and model as shown in FIG. 8.

Simulations were mostly carried out in 1D. Particles are assumed point particles with no in-between interaction. A large number of particles are placed randomly, following a uniform distribution over $[-A,A]$. In each time step $\Delta t$, particles move randomly, with the increments taken from a normal distribution with mean zero and variance $2D\Delta t$. If a proposed position was larger in magnitude than A, say $A+\in$, it was mirrored back to $A-\in$ (and likewise for $-A$). The code was run in Matlab 7.5.0 with the standard Marsaglia ziggurat algorithm for generating pseudo-random normally distributed numbers. The frequencies of particle trajectories with different numbers of consecutive positions in the observation volume were counted. The same particle was allowed to enter the field of view several times. Simulations were carried out in 3D to validate the simplification of the model from 3D to 1D. The characteristics were similar apart from the two additional independent diffusive components.

The depth of focus is the distance from the nearest objects in focus to the most distant objects in focus. The depth of focus is determined by the distance between the focal plane and the lens, the focal length and numerical aperture of the lens, and characteristics of the optical imaging system, e.g. the CCD sensor, with which image data are acquired. A more relevant measure the length of the interval parallel to the optical axis in which particles can be tracked; for this one the term tracking depth is coined.

Suppose that one has a monodisperse ensemble of particles in liquid dispersion with known diffusion coefficient. Given a value of the tracking depth, corresponding to 2a, the model gives the ideal probabilities for particles to be tracked during certain trajectory lengths. One can construct a maximum likelihood estimator â of a and fit the model to relative frequencies of trajectory lengths. Suppose one has observed particle trajectory lengths in the range $\{k_{min}, \ldots, k_{max}\}$. The number of trajectories of length k observed is $N_k$. The likelihood function $L(a;A,\Delta t,\sigma,\{N_k\}_{k=k_{min}}^{k_{max}})$ is the product of probabilities evaluated at the observed data points, i.e.

$$L(a) = \prod_{k=k_{min}}^{k_{max}} P_a(K=k)^{N_k} \quad [10]$$

with corresponding log likelihood $$l(a) = \sum_{k=k_{min}}^{k_{max}} N_k \log P_a(K=k). \quad [11]$$

Now the maximum likelihood estimator is defined as $$\hat{a} = \arg\max l(a). \quad [12]$$

Asymptotic theory for maximum likelihood estimators provides for a way of acquiring analytic confidence intervals easily. The sampling distribution is asymptotically normal, $$\hat{a} \sim N(a, I(a)^{-1}) \quad [13]$$

Where I(a) is the observed Fisher information and equal to $$I(a) = -\frac{d^2}{da^2} l(a). \quad [14]$$

Approximating I(a) by I(â), a 100(1-a) % confidence interval for a can be written $$\hat{a} \pm \lambda_{\alpha/2} I(\hat{a})^{-1/2} \quad [15]$$

where $\lambda_{\alpha/2}$ is the $\alpha/2$ quantile of the standard normal distribution. In this particular case, the observed Fished information is evaluated by standard finite difference approximations.

The proposed estimator and its associated confidence interval is validated on simulated data. Letting a=0.65, A=60, Δt=21.6 and D=3, 100 simulations is performed. The lower threshold $K_{min}$ was set to 3. The result show that the estimator is approximately unbiased, and that the confidence level of the confidence intervals is approximately correct.

Figure 9:
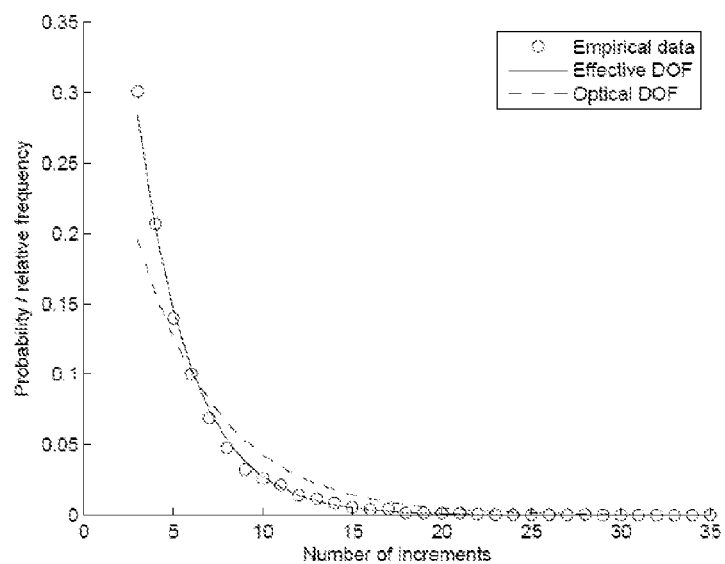
FIG. 9 illustrates a comparison of the models ability to capture the features of the empirical data using the optical depth of focus and the effective depth of focus, illustrating advantages of embodiments of the present invention.
Figure 9:
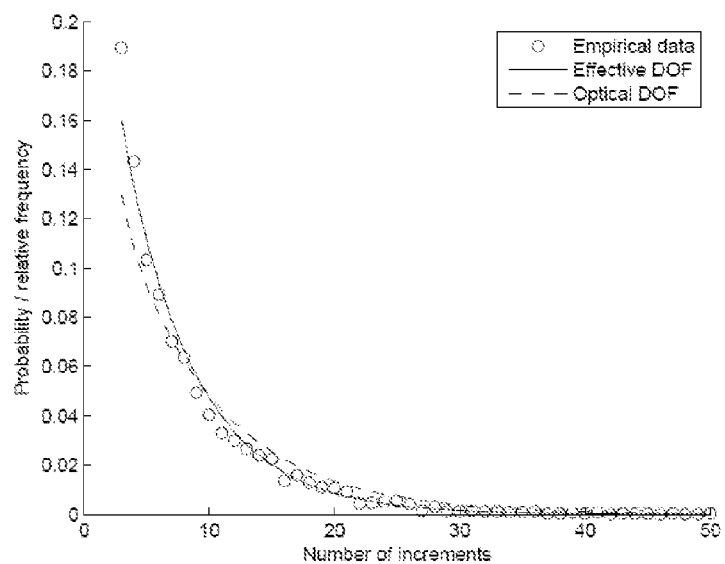

Experimental results were obtained. Yellow-green fluorescent carboxylated polystyrene nanospheres of nominal size 100 nm and 200 nm (Invitrogen, Merelbeke, Belgium), respectively, and a spread of about 5%, have been tracked using a custom developed single particle tracking setup with a wide-field laser illumination device for excitation and an electron-multiplying CCD sensor for video sequence acquisition. The optical definition of depth of focus gives that this is equal to 1.3 μm, corresponding to an a value of 0.65 μm. The thickness of the liquid dispersion in the optical axis direction is 120 μm, corresponding to A=60 μm. The time lapse was Δt=21.6 ms. Two data sets were used, with particles of approximately 100 nm and 200 nm diameter, respectively. The diffusion coefficients of the two data sets have been set to their respective average diffusion coefficients, 3.024 and 1.537 μm/s$^2$, as estimated from all the sampled particle trajectories. This is sensible, since all estimates irrespective of trajectory length are unbiased, apart from negligible measurement error. FIG. 9 illustrates that the observed trajectory length distribution can be explained by the proposed model when taking into account an effective depth of focus (DOF) rather than the theoretically expected value. In other words, fitting of the proposed model to the experimentally observed trajectory length distribution allows to estimate the effective DOF, i.e. the tracking depth parameter a.

Figure 10:
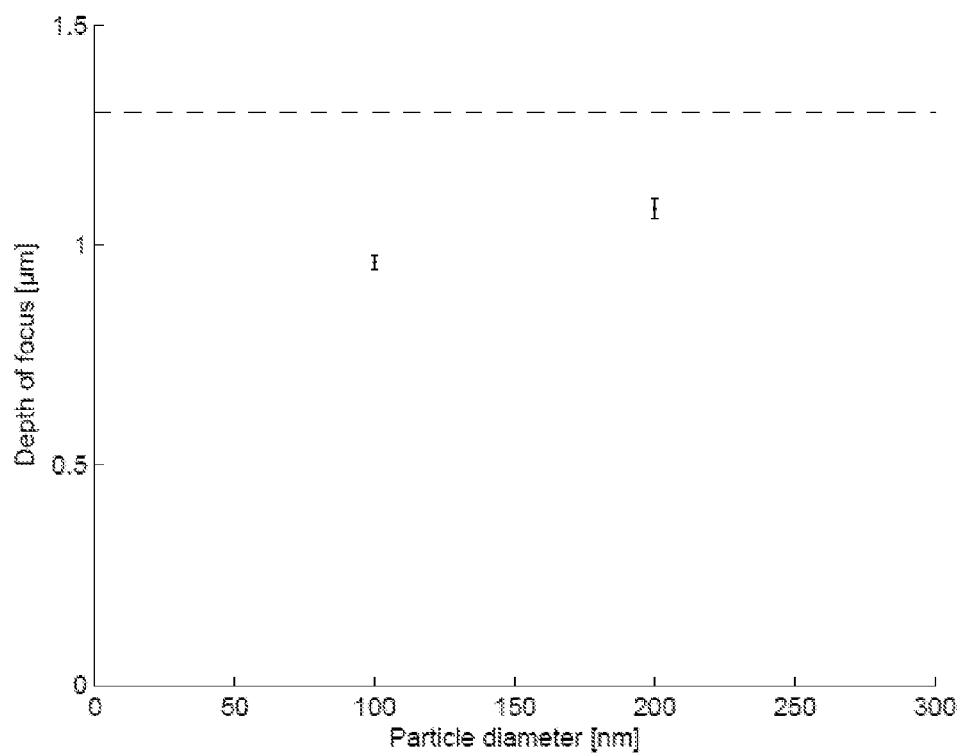
FIG. 10 illustrates an effective depth of focus as function of the particle diameter, the dashed line representing the optical depth of focus, illustrating features of embodiments according to the present invention.

Maximum likelihood estimation of a gives â=0.48 μm and a 95% confidence interval [0.4712 μm; 0.4890 μm] for 100 nm particles and â=0.5414 μm and a 95 confidence interval [0.5301 μm; 0.5528 μm] for 200 nm particles. This corresponds to a tracking depth of 0.9602 μm and a 95% confidence interval [0.9424 μm; 0.9780 μm] for 100 nm particles and 1.0828 μm and a 95% confidence interval [1.0602 μm; 1.1056 μm] for 200 nm particles. The latter also is illustrated in FIG. 10. The above simplified model illustrates the capability of describing the trajectory length distribution as function of the diffusion coefficient and the tracking depth as well as the observed distribution of diffusion coefficients as a function of the actual distribution.

The model has thus been validated against simulations and empirical data, consisting of several data sets of latex nanospheres of different diameter, tracked in liquid dispersion using laser illuminated wide-field microscopy. The model was in good agreement with empirical data, and manages to capture the essential features correctly.

Whereas the example indicated above has been described with reference to a maximum likelihood estimator, the model could for example also be worked out with a non-linear least squares estimator.

The development of this exemplary model is of interest for both 2D and 3D tracking of particles, where sampling effects caused by particles randomly moving in and out of focus are present. It is to be noticed that where the above example refers to effective depth of focus for the one dimensional model described, this can be mutatis mutandis extended to an effective volume in a three dimensional model.

Whereas for the exemplary model described above several approximations have been made, such approximations could be avoided, at the cost of a more complex model. One approximation that has been made is the omission of the fact that a small proportion of the particles are already in focus when the tracking is started, and hence do not follow the distribution of trajectory length described. Likewise, the fact that some particles may be in focus when the tracking stops is ignored. If the video sequence is not very short, these temporal edge effects will be negligible, and have been found to be negligible for the typical video sequence lengths used in the empirical data used herein. Correcting for these, if necessary, is a rather simple matter and could for example be performed using the assumption of initially uniform distribution in the beginning, and doing likewise in the end by a 'time mirroring' argument. Another simplification is to neglect bias effects that cannot be modeled by any physical means. For instance, measurement error caused by imprecise particle positioning can cause biases in diffusion coefficient estimation, although this should be negligible compared to the inherent statistical error of diffusion coefficient estimation by mean squared deviation. Additionally, it would be possible that small particles are more likely to be regarded as noise (and vice versa) than larger particles, and also that short trajectories are regarded as insignificant noise and that long trajectories are cut off into shorter ones due to failure in between-frame position matching. The effect of such biases would most likely be insignificant in most experimental settings.

Instead of using the distribution of trajectory lengths to fit the model to empirical data and estimate the tracking depth, it would in principle be possible to use the model for the observed distribution of diffusion coefficients instead. This would require monodisperse data sets of different diffusion coefficients with very precise knowledge of the concentration of particles.

Figure 11:
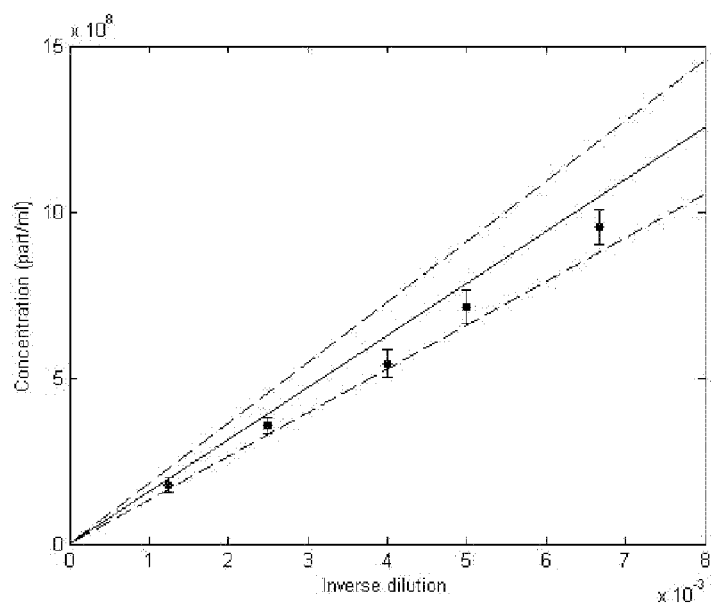
FIG. 11 and FIG. 12 illustrate the concentration of a series of dilutions for a 0.52 µm nanosphere respectively 0.19 µm nanosphere suspension, determined using a single particle tracking method according to an embodiment of the present invention.

By way of example, illustrative experiments indicating features and advantages of embodiments of the present invention are shown below. Two experiments are discussed for the single particle tracking method. In a first experiment, a water stock suspension containing 0.52 μm "dragon green" (excitation 480 nm, emission 520 nm) fluorescent polymer nanospheres (Bangs Laboratories, Fishers, USA) was diluted to a factor of 143, 191, 238, 413 and 751 times. Single particle tracking experiments were carried out on each dilution and the concentration was calculated using the first single particle tracking method. The time interval between the frames was Δt=58 ms and 40 videos of 10 s were acquired for every dilution. For each dilution all movies were analyzed with the single particle tracking method to obtain the number concentration. FIG. 11 illustrates the concentration of a series of dilutions of the 0.52 μm nanosphere suspension. The theoretical values (solid line) of the concentration with 95% confidence intervals (dashed line) and the single particle tracking values (dots) of the concentration with 95% confidence intervals (error bars) are shown in function of the dilution factor. The experimental concentrations correspond very well with the theoretical expectation within the confidence intervals for the different dilutions. The theoretical number concentration N (#/ml) is calculated based on the following formula:

$$N = \frac{6 \times 10^{10} S r_L}{p r_S d^3} \qquad [16]$$

wherein S=1 (the weight percentage of solids, with a relative standard deviation of 5% according to the manufacturer), $\rho_L$=1 (the density of the solvent in g/ml), $\rho_S$=1.05 (the density of the solid polystyrene particles in g/cm$^3$), d=0.497 (the mean diameter measured with dynamic light scattering in μm with a standard deviation of 0.09 μm).

Figure 12:
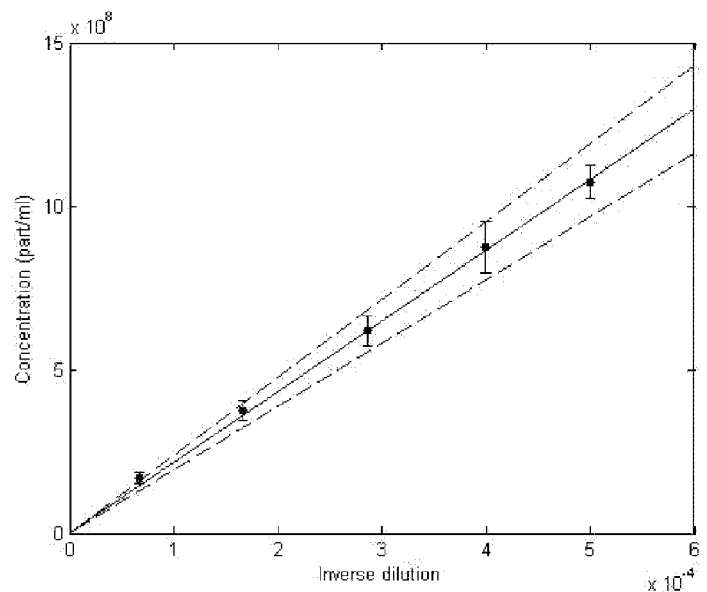

In a second experiment, a water stock suspension containing 0.19 μm "dragon green" (excitation 480 nm, emission 520 nm) fluorescent polymer nanospheres (Bangs Laboratories, Fishers, USA) was diluted to a factor of 1888, 2382, 3368, 5826 and 14753 times. Single particle tracking experiments were carried out on each dilution and the concentration was calculated using the first method based on particle trajectories. The time interval between the frames was Δt=38 ms and 40 videos of 10 s were acquired for every dilution. For each dilution all movies were analyzed with the single particle tracking method to obtain the number concentration. The resulting concentrations, together with the theoretically expected values, are shown in FIG. 12. More particularly, FIG. 12 illustrates the concentration of a series of dilutions of the 0.19 μm nanosphere suspension. The theoretical values (solid line) of the concentration with 95% confidence intervals (dashed line) and the single particle tracking values (dots) of the concentration with 95% confidence intervals (error bars) as function of the dilution factor. The experimental concentrations correspond very well with the theoretical expectation within the confidence intervals for the different dilutions. The theoretical number concentration N (#/ml) was again calculated from the formula [16] used in the first experiment, wherein d equaled 0.207 (the mean diameter measured with dynamic light scattering in μm with a standard deviation of 0.08 μm).

By way of illustration, embodiments of the present invention not being limited thereto, a model of a second exemplary method according to an embodiment of the present invention is described below. Embodiments of the present invention are also not limited to or restricted by the mathematical formalism used for illustration. Furthermore, illustrative experimental results also are discussed.

In the present illustration, what is described is the method of determination of effective observation volume by means of the time-dependent number of particles in the effective observation volume as determined from a time-series of observations, such as but not being limited to counting the number of particles within the observation volume in each frame of a time-lapse video. The stochastic process X(t) representing the particle count data, or number of particles in some observation volume, as a function of time is commonly referred to as a Smoluchowski process.

The number of particles in a rectangular observation volume of unknown axial dimension and known lateral dimensions is assumed to be observed at equidistant time points. The discrete-time Smoluchowski process is approximated by a Markov chain, although the process is only approximately Markovian even for Brownian particles.

Consider a dispersion of particles in a fluid, in the approximate center of which a box-like effective observation volume is situated. The lateral dimensions of the box are determined by the field of view and are thus assumed to be known already, and the axial dimension is assumed to be unknown, comprising the distance from the nearest detectable particle to the most distant detectable particle. Let a set of particles diffuse freely within the liquid dispersion, independent of one another on account of a sufficiently low concentration, and reflect against the walls. It is assumed that an estimate of the diffusion coefficient for the ensemble of particles is already available by any means of prior knowledge or by independent experimental determination. Assume a video sequence is acquired, detecting the particles within the observation volume at equidistant time points with sampling interval Δt. Assume further that one can determine the number of observed particles in each frame of the video sequence.

The Smoluchowski process X(t) is observed in diffusion equilibrium at equidistant time points nΔt, n=0, 1, 2, .... Let $X_n$=X(nΔt) be the observations, i.e. the number of particles residing within the observation volume at time nΔt is $X_n$. One wants to formulate a model relating the number of particles $X_{n+1}$ residing in the observation volume at time (n+1)Δt to $X_n$.

The Smoluchowski process can be described as an M/G/∞ queue (the number of particles entering is to extremely good approximation Poisson distributed, thereby the "M"; the life time within the observation volume (or in queuing theory, service time) of each particle follows a general distribution which is typically not exactly known, thereby the "G"; and there are an infinite number of servers, meaning here that particles are independent, thereby the "∞"). This G corresponds to the trajectory length distribution which in general does not have a simple analytical form. The distribution G is in this illustrative example approximated by an exponential distribution, hence assuming an M/M/∞ model.

The number of particles entering the observation volume in each time step (i.e. between consecutive frames) follows to very close approximation a Poisson distribution. The particle trajectory length distribution is approximately geometric in discrete time (using the M/M/∞ model) and hence, the number of particles exiting the observation volume is binomially distributed in every time step, i.e.

$$X_{n+1} = X_n + I_n - O_n, \quad [17]$$

where $I_n$ is the number of particles entering the observation volume during the interval (nΔt,(n+1)Δt) and is Poisson distributed with unknown parameter λ. $O_n$ is the number of particles (out of the $X_n$ particles which are present) that exits the observation volume in (nΔt,(n+1)Δt) and is, conditionally on $X_n$=i, binomially distributed with index i and unknown parameter μ. Note that by assumption of thermal equilibrium, the Markov chain is in its stationary (equilibrium) distribution already from the start. This constitutes a Markov chain with transition probabilities $p_{ij}(\lambda,\mu)=P(X_{n+1}=j|X_n=i)$, where $$p_{ij}(\lambda, \mu) = e^{-\lambda} \sum_{k=max(0,j-i)}^{j} \frac{\lambda^k}{k!} \binom{i}{i-j+k} \mu^{i-j+k}(1-\mu)^{j-k}, \quad [18]$$

For i≥0 and j≥0

Observe that the joint density of observations $x_1, \ldots, x_n$ from one video sequence can under the model assumption be written $$P(x_1, \ldots, x_n) = P(x_1)P(x_2|x_1)P(x_3|x_2) \ldots P(x_n|x_{n-1}). \quad [19]$$

This can hence be regarded as one observation from the initial (stationary) distribution and n−1 observations from the set of transition probability distributions. In this example consider only the transition probabilities and define the loglikelihood function to be $$L(\lambda,\mu) = \Sigma_{i,j} N_{ij} \log(p_{ij}(\lambda,\mu)) \quad [20]$$

Where $N_{ij}$ the observed number of transitions from state i to state j. Only the transition probabilities in the loglikelihood are kept since they dominate the first term for large n. This generalizes without effort to the more typical case in experimental situations, where data are acquired not from one sequence but from several independent sequences corresponding to different videos. This does not change the structure of the loglikelihood function, only the counts $N_{ij}$.

One gets maximum likelihood estimates $\hat{\lambda}$ and $\hat{\mu}$ as the maximizers of the loglikelihood function in the region $0<\lambda<\infty, 0<\mu<1$.

Now, $\mu$ equals the probability $$P_{exit}(a) = 1 - \quad [21]$$

$$\frac{(2D\Delta t)^{\frac{3}{2}}}{8 a_x a_y a} \left( \frac{2a_x}{\sqrt{2D\Delta t}} \left( 2\Phi\left(\frac{2a_x}{\sqrt{2D\Delta t}}\right) - 1 \right) + 2\varphi\left(\frac{2a_x}{\sqrt{2D\Delta t}}\right) - 2\varphi(0) \right) *$$

$$\left( \frac{2a_y}{\sqrt{2D\Delta t}} \left( 2\Phi\left(\frac{2a_y}{\sqrt{2D\Delta t}}\right) - 1 \right) + 2\varphi\left(\frac{2a_y}{\sqrt{2D\Delta t}}\right) - 2\varphi(0) \right) *$$

$$\left( \frac{2a}{\sqrt{2D\Delta t}} \left( 2\Phi\left(\frac{2a}{\sqrt{2D\Delta t}}\right) - 1 \right) + 2\varphi\left(\frac{2a}{\sqrt{2D\Delta t}}\right) - 2\varphi(0) \right)$$

which is the probability that a random (uniformly distributed) particle exits the observation volume. Here D is a diffusion coefficient assumed common to all particles under study, $a_x$ and $a_y$ are the lateral dimensions of the effective observation volume, and a is the axial dimension of the effective observation volume (and hence the only unknown). Functions $\phi$ and $\Phi$ are the density function and cumulative distribution function, respectively, of the standard normal distribution, i.e.

$$\varphi(z) = \frac{1}{\sqrt{2\pi}} e^{-\frac{1}{2}z^2} \quad [22]$$

and $$\Phi(z) = \int_{-\infty}^{z} \varphi(t) dt \quad [23]$$

Figure 13:
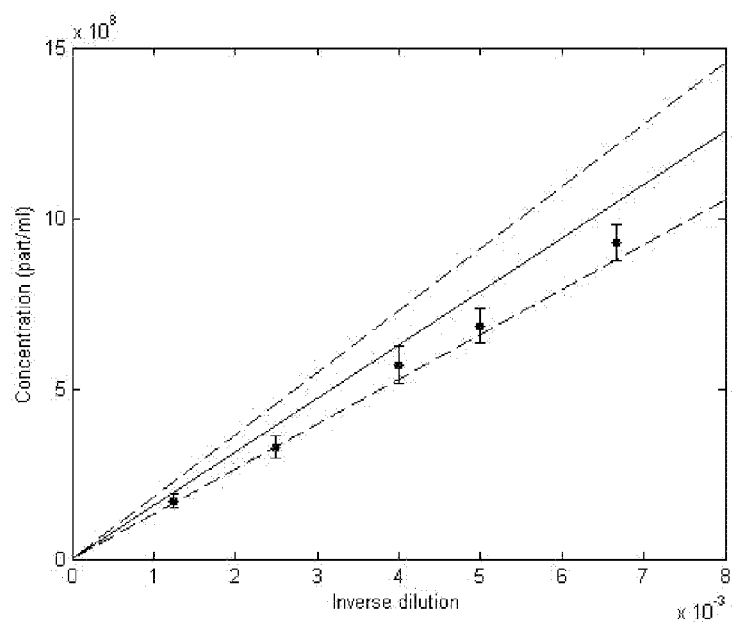
FIG. 13 and FIG. 14 illustrate the concentration of a series of dilutions for a 0.52 µm nanosphere respectively 0.19 µm nanosphere suspension, determined using a Smoluchowski-based method according to an embodiment of the present invention.
Figure 14:
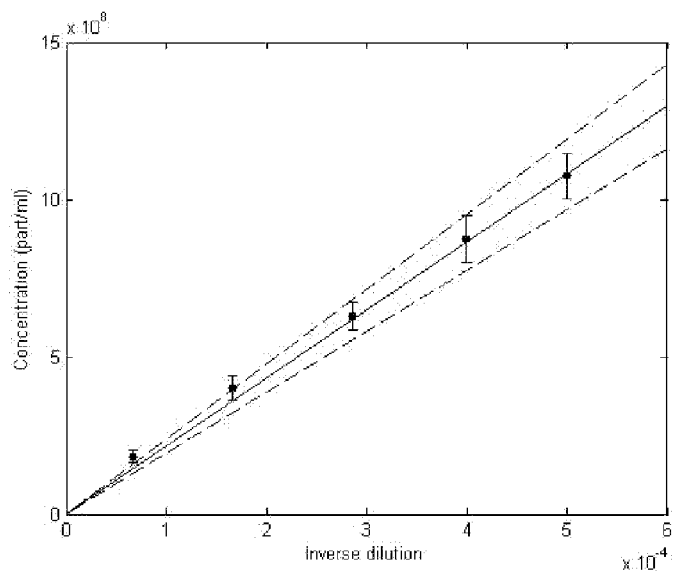

This can be used to estimate the tracking depth (equal to 2a) and effectively the size of the observation volume, since one can find an estimate $\hat{a}$ of a by solving for a in the relation $P_{exit}(a)=\hat{\mu}$ This provides the means to determine the size of the effective observation volume and subsequently number concentration. By way of example, also illustrative experimental results are provided, indicating features and advantages of the Smoluchowski based embodiments of the present invention. The same dataset as used for the single particle tracking method described above (i.e. based on 0.19 μm diameter nanospheres and 0.52 μm diameter nanospheres) was analysed using the Smoluchowski method. The resulting concentrations together with the theoretically expected values are shown in FIG. 13 and FIG. 14. In FIG. 13, the concentration of a series of dilutions of the 0.52 μm nanosphere suspensions is shown. The theoretical values (solid line) of the concentration with 95% confidence intervals (dashed line) and the Smoluchowski values (dots) of the concentration with 95% confidence intervals (error bars) are shown as function of the dilution factor. In FIG. 14, the concentration of a series of dilutions of the 0.19 μm nanosphere suspension is shown. The theoretical values (solid line) of the concentration with 95% confidence intervals (dashed line) and the Smoluchowski values (dots) of the concentration with 95% confidence intervals (error bars) are shown as function of the dilution factor. The experimental concentrations for both sizes correspond very well with the theoretical expectation within the confidence intervals for the different dilutions. Comparing FIG. 11 with FIG. 13 and FIG. 12 with FIG. 14, it is clear that the first single particle tracking method and the second Smoluchowski method agree closely with each other.

By way of illustration, also a further example is provided illustrating a correction for the so called and so previously denoted sampling bias effect. The sampling bias effect affects the estimation of a (polydisperse) distribution of diffusion coefficients using SPT. This is a shortcoming of SPT (concentration) measurements based on the number of trajectories that was recognized earlier. Without a suitable correction this will lead to a biased concentration measurement (sampling bias). If all trajectories are included in the measurement, the number of fast moving particles are overestimated compared to the number of more slowly moving particles. If only trajectories of length above a certain threshold (the minimum trajectory length) are included in the measurements, it may also be the case that the number of slowly moving particles are overestimated compared to the number of more quickly moving particles, since a large proportion of the trajectories for the more quickly moving particles will be disregarded.

Without wishing to be bound by theory, the effect could be understood from the following theoretical considerations. Assume that the distribution of true diffusion coefficients is a Dirac mixture (discrete mixture) of/components with diffusion coefficients $D_1, D_2, \ldots, D_I$ written $$f_D(x) = \sum_{i=1}^{I} \theta_i \delta(x - D_i) \quad [24]$$

where $\theta_i$ are the mixing coefficients (proportions, probabilities) and $\delta$ is the Dirac delta function. An algorithm for the estimation of such discrete probability distributions of diffusion coefficients is known in the art and does not as such constitute part of the present invention.

Let E be the event that a particle enters the detection region, and let D be the event that a particle has diffusion coefficient D. Given a diffusion coefficient D, the probability of a particle, uniformly distributed over the suspension but not present in the detection region, to enter the detection region is $$P(E \mid D) = \frac{1}{A-a} \quad [25]$$

$$\left[ (A+a)\Phi\left(\frac{A+a}{\sqrt{2D\Delta t}}\right) - (A-a)\Phi\left(\frac{A-a}{\sqrt{2D\Delta t}}\right) - 2a\Phi\left(\frac{2a}{\sqrt{2D\Delta t}}\right) \right] +$$

$$\frac{\sqrt{2D\Delta t}}{A-a} \left[ \phi\left(\frac{A+a}{\sqrt{2D\Delta t}}\right) - \phi\left(\frac{A+a}{\sqrt{2D\Delta t}}\right) - \phi\left(\frac{2a}{\sqrt{2D\Delta t}}\right) + \phi(0) \right]$$

using the same one-dimensional approximation of the liquid suspension and the detection region as previously described. For experimental SPT data of diffusing particles, it is typical to impose a lower threshold for the trajectory length. Let T be the event that a particle is tracked, i.e. that it enters the detection region and additionally that its trajectory length is at least a minimum trajectory length $k_{min}$. Let once again D be the event that a particle has diffusion coefficient D. The probability of tracking the particle is $$P(T|D) = P(E|D) P(K \geq k_{min} | D, E) \quad [26]$$

Note that the dependency of the tracking probability on the particle diffusion coefficient is here explicitly stated. Now consider a polydisperse set of particles with a finite set of diffusion coefficients $D_1, D_2, \ldots, D_I$. If one knows, hypothetically, the true distribution, i.e. the probabilities $P(D_1), P(D_2), \ldots, P(D_j)$, one can express the observed distribution of diffusion coefficients by Bayes' theorem, since $$P(D_i | T) = \frac{P(T | D_i)P(D_i)}{\sum_j P(T | D_j)P(D_j)} \quad [27]$$

In words, the probability is expressed that a randomly chosen tracked particle has diffusion coefficient $D_i$, in terms of the probabilities $P(T|D_j)$ that a random particle with diffusion coefficient $D_j$ is tracked and the probability distribution $P(D_j)$ over the different diffusion coefficients. This is valid for all i, and the values $P(T|D_i)$ are computed using Equation [26]. And if, conversely, the observed distribution of diffusion coefficients is known, i.e. the probabilities $P(D_1|T), P(D_2|T), \ldots, P(D_j|T)$, the true distribution from the relation can be retrieved by $$P(D_i) = \frac{1}{Z} \frac{P(D_i | T)}{P(T | D_i)} \quad [28]$$

where $$Z = \frac{1}{\sum_j P(T | D_j)P(D_j)} \quad [29]$$

or alternatively $$Z = \sum_j \frac{P(D_j | T)}{P(T | D_j)} \quad [30]$$

which can be obtained from Equation [28] by multiplying with Z and summing over i. The probabilities $P(D_i|T)$ would typically not be exactly known, but estimated in a SPT sizing experiment and directly corresponding to the $\theta_i$ as defined earlier. The probability $P(D_i|T)$ hence corresponds to the probability that an observed particle trajectory has diffusion coefficient $D_i$, rather than the probability that a physical particle in the dispersion has diffusion coefficient $D_i$. The probabilities $P(T|D_j)$ can be computed using Equation [26] and thereby also Equation [25]. Since Equation [25] explicitly depends on the tracking depth a, also $P(T|D_j)$ depends on the tracking depth parameter a (and hence the observation volume). Therefore, it is essential to know the effective observation volume in order to correct for the sampling bias effect. The sampling bias can now be removed from an experimentally obtained distribution of diffusion coefficients using Equation [28].

Figure 15:
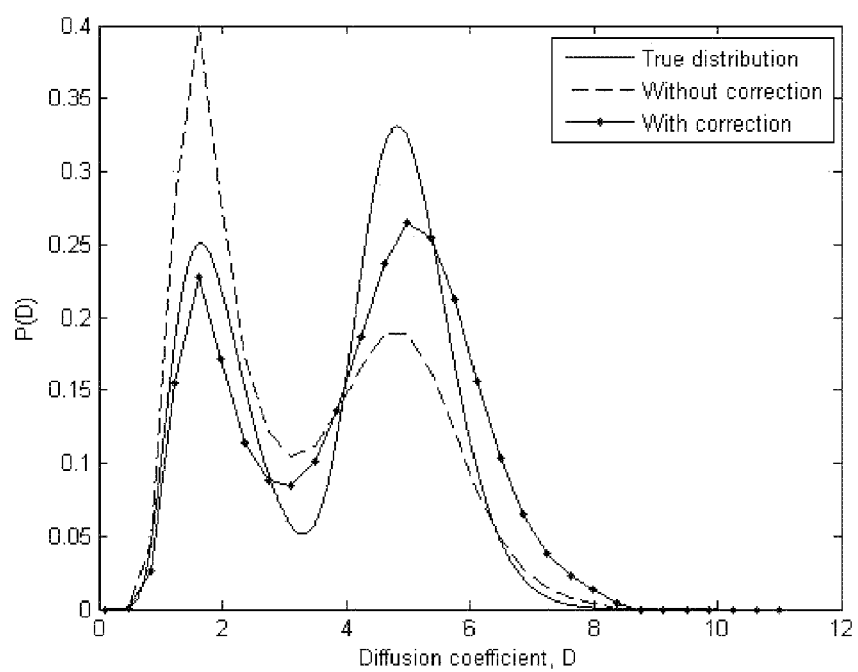
FIG. 15 illustrates the theoretical distribution, calculated distribution and the distribution after correction for sampling bias, according to an embodiment of the present invention. The drawings are only schematic and are non-limiting. In the drawings, the size of some of the elements may be exaggerated and not drawn on scale for illustrative purposes.

The correction is further illustrated by one simulation of particles from a distribution of diffusion coefficients which is a mixture of two lognormal distributions. The simulation was performed in the following fashion. A large number of particles (1000) was placed randomly in a virtual liquid suspension of size 100×100×100 µm. Randomly selected diffusion coefficients from the mixture of two lognormal distributions were assigned to the particles, and random normally distributed increments were simulated. The particles were "tracked" in the virtual detection region having a size of 50×50×2 µm, centered in the virtual liquid suspension. The observed trajectories were used to estimate the distribution of (observed) diffusion coefficients using an algorithm described in Braeckmans et al. Nano Letters 10, (2010). Drawn in FIG. 15 is the true distribution, the distribution of observed diffusion coefficients and the distribution of the observed diffusion coefficients after correction for the sampling bias using the above described model (denoted "with correction").

The invention claimed is:

1. A method for determining a size or shape related parameter of an effective observation volume for an observation technique for particles undergoing at least partially stochastic motion in a dispersion, based on a time-series of observations, comprising:
   detecting the particles of the dispersion in the effective observation volume to obtain a time-series of observations of the particles,
   determining one or more time-dependent characteristics of the dispersion or the particles, based on the obtained time-series of observations,
   determining at least one stochastic motion-related parameter representative for the at least partially stochastic motion of at least one particle in the dispersion,
   determining a size or shape related parameter of the effective observation volume by modeling of the at least partially stochastic motion of the particle movement in the dispersion, the modeling taking into account the at least one stochastic motion-related parameter and the determined one or more time-dependent characteristics, wherein the size or shape related parameter of the effective observation volume at least takes into account the distance from a nearest detectable particle to a most distant detectable particle in the effective observation volume, and
   determining a concentration of particles in the dispersion based on the size or shape related parameter of the effective observation volume and the one or more characteristics.

2. The method according to claim 1, wherein determining the concentration of particles comprises determining the concentration as a function of the at least one stochastic motion-related parameter or a parameter derived therefrom.

3. The method according to claim 1, wherein determining one or more time-dependent characteristics comprises
   determining from the time-series of observations trajectories for individual particles in the dispersion, and
   determining the distribution of number of trajectories versus particle trajectory length, and
   wherein determining a size or shape related parameter of the effective observation volume comprises modeling the at least partially stochastic motion of the particle movement in the dispersion based on the at least one stochastic motion-related parameter and the trajectory length distribution.

4. The method according to claim 1, wherein determining one or more characteristics comprises determining a number of particles in observation in at least two different points in time.

5. The method according to claim 1, wherein the motion-related parameter is a diffusion coefficient.

6. The method according to claim 2, wherein determining the concentration of particles comprises determining the concentration of particles inherently taking into account the effective observation volume in a calibration free manner.

7. The method according to claim 3, wherein the at least one stochastic motion-related parameter is determined from the trajectory of at least one particle.

8. The method according to claim 3, comprising determining the concentration of particles in the dispersion based on the number of trajectories and the size or shape related parameter of the effective observation volume.

9. The method according to claim 4, comprising determining the number concentration of particles in the dispersion based on the number of particles in observation and the effective observation volume.

10. A system for determining a size or shape related parameter of an effective observation volume for an observation technique for particles undergoing at least partially stochastic motion in a dispersion based on a time-series of observations, comprising:
- an input arrangement arranged to receive one or more time-dependent characteristics of the dispersion or its particles based on the time-series of observations,
- a processor configured to determine at least one stochastic motion-related parameter representative for the at least partially stochastic motion of at least one particle in the dispersion and to determine a size or shape related parameter of the effective observation volume by modeling of the at least partially stochastic motion of the particle movement in the dispersion, the modeling taking into account the at least one stochastic motion-related parameter and the determined one or more time-dependent characteristics, wherein the size or shape related parameter of the effective observation volume at least takes into account the distance from a nearest detectable particle to a most distant detectable particle in the effective observation volume, and
- wherein the processor is also configured to determine the concentration of particles in the dispersion based on the size or shape related parameter of the effective observation volume and the one or more time-dependent characteristics.

11. The system according to claim 10, wherein the processor is configured to determine the concentration as a function of the at least one stochastic motion-related parameter or a parameter derived therefrom.

12. The system according to claim 10, wherein the processor is configured to determine from the time-series of observations trajectories for individual particles in the dispersion, and to determine the distribution of number of trajectories versus particle trajectory length, and
- wherein the processor is arranged to model the at least partially stochastic motion of the particle movement in the dispersion, the modeling taking into account at least one stochastic motion-related parameter and the trajectory length distribution to determine the size or shape related parameter of the effective observation volume.

13. The system according to claim 10, wherein the processor is configured to determine one or more characteristics by determining a number of particles in the effective observation volume at at least two different points in time.

14. The system according to claim 10, wherein the system is configured to determine a diffusion coefficient.

15. A system according to claim 10, wherein the system is implemented as a computer program product for, when executing on a computer, performing a method for determining a concentration of nanoparticles in a dispersion.

16. The system according to claim 12 wherein the processor is configured to determine the at least one stochastic motion-related parameter from the trajectory of at least one particle.

17. The system according to claim 12, wherein the processor furthermore is arranged to determine the concentration of particles in the dispersion based on the number of trajectories and the size or shape related parameter of the effective observation volume.

18. The system according to claim 13, the processor being configured to determine the concentration of particles in the dispersion based on the number of particles in observation and the size or shape related parameter of the effective observation volume.

19. A method for determining a size or shape related parameter of an effective observation volume for an observation technique for particles undergoing at least partially stochastic motion in a dispersion, based on a time-series of observations, comprising:
- detecting the particles of the dispersion in the effective observation volume to obtain a time-series of observations of the particles, wherein the step of detecting the particles of dispersion to obtain the time-series of observations comprises capturing a plurality of images of the particles in a time sequence,
- determining one or more time-dependent characteristics of the dispersion or the particles, based on the obtained time-series of observations,
- determining at least one stochastic motion-related parameter representative for the at least partially stochastic motion of at least one particle in the dispersion, and
- determining a size or shape related parameter of the effective observation volume by modeling of the at least partially stochastic motion of the particle movement in the dispersion, the modeling taking into account the at least one stochastic motion-related parameter and the determined one or more time-dependent characteristics, wherein the size or shape related parameter of the effective observation volume at least takes into account the distance from a nearest detectable particle to a most distant detectable particle in the effective observation volume, and
- determining a concentration of particles in the dispersion based on the size or shape related parameter of the effective observation volume and the one or more characteristics.

20. The method of claim 19, wherein said plurality of images is determined at a plurality of points of time of 10 or more.

* * * * *